United States Patent

Kiesewetter et al.

[11] Patent Number: 5,938,907
[45] Date of Patent: *Aug. 17, 1999

[54] METHOD FOR RECOVERING GUANIDINE SALTS

[75] Inventors: Erwin Kiesewetter, Stolberg; Klaus Peter Stengele, Ampfing, both of Germany

[73] Assignee: NIGU Chemie GmbH, Waldkraiburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/696,820

[22] PCT Filed: Feb. 21, 1995

[86] PCT No.: PCT/EP95/00629

§ 371 Date: Aug. 20, 1996

§ 102(e) Date: Aug. 20, 1996

[87] PCT Pub. No.: WO95/22398

PCT Pub. Date: Aug. 24, 1995

[30] Foreign Application Priority Data

Feb. 22, 1994 [DE] Germany ............... 44 05 546

[51] Int. Cl.⁶ .................................................... B01D 61/44
[52] U.S. Cl. .......................... 204/530; 204/541; 204/544
[58] Field of Search ................................... 204/530, 541, 204/544

[56] References Cited

U.S. PATENT DOCUMENTS

| 4,157,348 | 6/1979 | Ono et al. ........................... 260/564 D |
| 4,260,644 | 4/1981 | Erikkson et al. ........................ 426/656 |
| 4,678,553 | 7/1987 | Mandle et al. ........................ 204/182.6 |

FOREIGN PATENT DOCUMENTS

| 2 198 705 | 4/1974 | European Pat. Off. . |
| 2 386 518 | 11/1978 | European Pat. Off. . |

OTHER PUBLICATIONS

Obering et al., "Elektrodialyse und Diffusionsdialyse," Technical Report of the FIGAWA Working Group 'Membrane Technology' (with English-language translation of pertinent parts).

*Primary Examiner*—Arun S. Phasge
*Attorney, Agent, or Firm*—Sughrue, Mion, Zinn Macpeak & Seas, PLLC

[57] ABSTRACT

A process for recovering guanidine salts from diluted and contaminated aqueous solutions is described, wherein the corresponding aqueous solution (diluate) is subjected to electrodialysis and the guanidine salt is concentrated on the concentrate side. The corresponding guanidine salt can thus largely be separated from all contaminants while a relatively highly concentrated product is simultaneously obtained.

13 Claims, No Drawings

METHOD FOR RECOVERING GUANIDINE SALTS

This application is a 371 of PCT/EP95/00629 filed Feb. 21, 1995.

The present invention relates to a method for recovering guanidine salts from diluted and contaminated aqueous solutions.

Guanidine salts represent important products in organic synthesis processes as well as in biotechnological processes. For this reason, large amounts of waste water result during the corresponding technical uses which can contain, aside from guanidine salts, numerous further contaminants of organic but also inorganic origin. In this manner, suitable guanidine salt solutions, such as they are used, for example, in chromatography, in the denaturation and/or renaturation of protein solutions or dissolution of inclusion bodies, are usually contaminated with residual proteins, reducing compounds (such as sulfides, for example), non-ionic detergents or buffer salts. Additionally, the concentration of guanidine salts is subject to very strong variations.

From an economic point of view, but also on the basis of environmental protection, great interest exists to isolate the respective guanidine salts and/or recover them again in a form which is as pure as possible. The only technical possibility offered thus far was to first concentrate diluted solutions and subsequently purify the guanidine salts by crystallization. The high energy expenditure which is necessary to evaporate, in part, large amounts of water is particularly disadvantageous in these methods. Additionally, the clean separation of the contaminants by crystallization causes considerable problems which is why multiple recrystallization is necessary for the recovery of somewhat pure products, and therefore this method seems rather technically complex.

Therefore, the object of the present invention was to develop a method for the recovery of guanidine salts from diluted and contaminated aqueous solutions which does not have the mentioned disadvantages of the prior art, but instead makes it possible to isolate guanidine salts in high purity from these solutions with little technical effort.

The object was solved according to the invention by subjecting the corresponding aqueous solution (diluate) to an electrodialysis and enriching the guanidine salts on the concentrate side in a concentrated form.

A detailed summary of the principle of electrodialysis and its use is found in J. Fritsch et al. "Electrodialysis and Diffusion Dialysis", Galvanotechnology, volume 7, 1991, Eugen G. Lenze Publisher, Saulgau.

Namely, it has been surprisingly shown that the corresponding guanidine salt can be considerably separated from all contaminants and a product can simultaneously be isolated in very high concentration (on the concentrate side).

From U.S. Pat. No. 4,678,553 a method is known for the recovery of polypeptides and proteins from solutions containing guanidine salts with the help of electrodialysis, however, in this case, the guanidine salts are present in a relatively concentrated form and are diluted in the course of the electrodialysis.

In the method commensurate with the present invention, guanidine salts solutions which partially have a concentration of <1% by weight, are electrodialysed. In this connection, practically all technically important salts can be used as guanidine salts, such as for example guanidine hydrochloride, sulfamate, phosphate, sulfate, thiocyanate or nitrate.

The electrodialysis itself can be carried out in technically customary electrodialysis cells which are equipped with known ion-selective membranes (essentially ion exchange membranes). With respect to the electrode rinse to be used, it has been proven to be particularly advantageous to rely on guanidine salts solutions such as guanidine phosphate or sulfate. In this manner, it is ensured that no undesired contaminants infiltrate into the concentrate.

The electrical parameters such as current density and voltage can vary in accordance with the technical possibilities of the electrodialysis cells. Normally, 200 to 1000 A/m$^2$, especially 300 to 700 A/m$^2$ electrode surface and voltages of approximately 0.5 to 3 volts per cell pair are technically appropriate.

In order to be able to obtain a somewhat satisfying throughput, a multitude of cell pairs are combined into so-called membrane stacks in a technically customary manner whose number usually is 5 to 500, preferably 300 to 400 cell pairs per stack.

The method according to the invention is practically carried out in a manner in which the diluted and contaminated aqueous solution (diluate) is continuously pumped into the cell pairs, the electrodialysis is carried out at desired current density and voltage and the concentrate with concentrated guanidine salts is continuously drawn off.

A particular advantage of the method according to the invention is that the electrodialysis can be carried out in a very wide pH-range which preferably is between 0 and 12 and is only dependent on the acid and base resistance of the membrane material used. This has the large advantage that the employed eluates can normally be used without intense pretreatment with acidic or alkali additives.

According to a preferred embodiment of the present invention, the electrodialysis is carried out in two or more steps, whereby the relevant membrane stack is connected in series, i.e. the concentrate from the first membrane stack is used as the diluate in the second membrane stack, etc. In this manner, a further concentration of the relevant eluates is possible. While the eluate in the first step is used, for example, with a concentration of <1% by weight with respect to the relevant guanidine salt, the concentrate after the first step already possesses a concentration of guanidine salt of 10 to 20% by weight; after the second step, 20 to 25% by weight. With the electrodialysis cells available at the present time, a concentration of the corresponding guanidine salt solutions is possible to maximally 25 to 50% by weight.

These concentrated solutions already have a very high purity which is >98% and usually has only small amounts of other salts. In case it is desired or required, a crystallization step can be linked up with the electrodialysis step in order to isolate the relevant salt in solid from.

Essentially, the particular advantages of the method according to the invention are that, when starting from a relatively highly diluted solution with highly variable contaminants, guanidine salts can be concentrated to a concentration of 35 to 50% by weight and the contaminants contained in the starting solutions can simultaneously be practically completely separated without large technical and energy expenses.

The following examples serve to more closely illustrate the invention.

EXAMPLES

Description of the Apparatus

The execution of the examples occurs in an electrodialysis device which was modified according to the patent claims in such a manner that 2 cell stacks were connected in series, each equipped with 7 cation selective membranes, 5 anionic selective membranes and 11 spacers (5 cell pairs in each case), a membrane distance of 0.5 mm and an effective cross-sectional area of 58 cm². Therewith, four circuits resulted which were separated from each other:

Diluate 1: the solution from which the salt should be recovered.
Concentrate 1: an intermediate solution in which a first step of concentration as well as the purification occurs.
Diluate 2: is equal to concentrate 1.
Concentrate 2: the solution in which the second step of the concentration occurs and the salt to be recovered is continuously removed by overflow.
Electrode rinse: a solution of chloride-free guanidine salts which should prevent development of chlorine gas on the anode from occurring.

Example 1

30 kg of a solution of guanidinium chloride from the production of a recombinant protein (diluate 1) are electrodialyzed in the above-mentioned apparatus for 83 hours. A constant maximal value of the current strength of 4 amperes is set in both circuits, whereby the voltage necessary for this is automatically regulated in accordance with the respective resistance of the cell stack, but is limited to a maximum of 12 volts. The product (concentrate 2) was collected in an overflow container. The electrodialysis was concluded when precipitates in diluate 1 reduced the flow rate to under 30% of the beginning value.

Starting conditions of the electrodialysis:

Diluate 1: see below
Concentrate 1: =diluate 2: 1% by weight aqueous solution of guanidinium chloride
Concentrate 2: 1% by weight aqueous solution of guanidinium chloride
Electrode rinse: 8% by weight aqueous solution of guanidinium dihydrogen phosphate

| parameter condition | diluate 1 | concentrate 2 |
| --- | --- | --- |
| Conductivity - start [mScm$^{-1}$] | 163 | 10 |
| Conductivity - finish [mScm$^{-1}$] | 105 | 190 |
| Guanidinium chloride - start [% by weight] | about 23 | 1 |
| Guanidinium chloride - finish [% by weight] | 9 | 46 |
| TRIS-buffer - start [mM] | about 25 | n. deter. |
| TRIS-buffer - finish [mM] | n. deter. | <1 |
| Dithioerythritol - finish [mM] | about 15 | not detectable |
| Glutathione - finish [mM] | about 15 | not detectable |
| EDTA - finish [mM] | about 7 | not determined |
| Proteins - finish [% by weight] | <0.5 | not detectable |
| Brij-35 - finish [% by weight] | <0.5 | not detectable |
| Iron - finish [mg/kg] | about 5 | <0.5 |

From the solution of concentrate 2, a technically pure guanidinium chloride (content>98.5% by weight) can be isolated by subsequent crystallization which is suitable for renewed use in the isolation of recombinant proteins.

Example 2

25 kg of a solution of guanidinium chloride from the production of a recombinant protein (diluate 1) were electrodialyzed in the above-mentioned apparatus for 50 hours. A constant maximal value of the current intensity of 3 amperes is set in both circuits, whereby the voltage necessary for this is automatically regulated in accordance with the respective resistance of the cell stack, but is limited to a maximum of 12 volts. The product (concentrate 2) was collected in a overflow container.

Starting conditions of the electrodialysis:

Diluate 1: see below
Concentrate 1: =diluate 2: 1% by weight aqueous solution of guanidinium chloride
Concentrate 2: 1% by weight aqueous solution of guanidinium chloride
Electrode rinse: 8% by weight aqueous solution of guanidinium dihydrogen phosphate

| parameter condition | diluate 1 | concentrate 2 |
| --- | --- | --- |
| Conductivity - start [mScm$^{-1}$] | 67 | 10 |
| Conductivity - finish [mScm$^{-1}$] | 0.2 | 147 |
| Guanidinium chloride - start [% by weight] | about 8 | 1 |
| Guanidinium chloride - finish [% by weight] | <0.5 | 42 |
| TRIS-buffer - start [mM] | about 25 | n. deter. |
| TRIS-buffer - finish [mM] | n. deter. | <1 |
| Sodium acetate - finish [% by weight] | 0.1 | 0.1 |
| Dithioerythritol - finish [mM] | about 15 | not detectable |
| Glutathione - finish [mM] | about 15 | not detectable |
| EDTA - finish [mM] | about 5 | not determined |
| Proteins - finish [% by weight] | <0.5 | not detectable |
| Benzamidine hydrochloride [% by weight] | 0.05 | 0.05 |
| Iron - finish [mg/kg] | about 2 | <0.5 |

From the solution of concentrate 2, a technically pure guanidinium chloride (content>98.5% by weight) can be isolated by subsequent crystallization which is suitable for renewed use in the isolation of recombinant proteins.

Example 3

2.5 kg of a solution of guanidinium thiocyanate of technically pure quality is electrodialyzed in the above-mentioned apparatus for 43 hours. A constant maximal value of voltage of 6 volts is set in both circuits, whereby the current intensity necessary for this is automatically regulated in accordance with the respective resistance of the cell stack, but is limited to a maximum of 3 amperes. The product (concentrate 2) was collected in an overflow container.

Starting conditions of the electrodialysis:

Diluate 1: see below
Concentrate 1: =diluate 2: 1% by weight aqueous solution of guanidinium thiocyanate
Concentrate 2: 1% by weight aqueous solution of guanidinium thiocyanate
Electrode rinse: 8% by weight aqueous solution of guanidinium dihydrogen phosphate

| parameter condition | diluate 1 | concentrate 2 |
| --- | --- | --- |
| Conductivity - start [mScm$^{-1}$] | 70 | <1 |
| Conductivity - finish [mScm$^{-1}$] | 2 | 135 |
| Guanidinium thiocyanate - start [% by weight] | about 7 | 1 |
| Guanidinium thiocyanate - finish [% by weight] | <0.3 | 17 |
| Iron - start [mg/kg] | about 5 | <0.1 |
| Iron - finish [mg/kg] | about 2 | <0.3 |

From the solution of concentrate 2, a technically pure guanidinium thiocyanate(content>99% by weight) can be isolated by subsequent crystallization which is suitable for renewed use in the isolation of recombinant proteins or for molecular biology.

Example 4

2.5 kg of a solution of guanidinium dihydrogen phosphate of technically pure quality is electrodialyzed in the above-mentioned apparatus for 73 hours. A constant maximal value of voltage of 12 volts is set in both circuits, whereby the current intensity necessary for this is automatically regulated in accordance with the respective resistance of the cell stack, but is limited to a maximum of 4 amperes. The product (concentrate 2) was collected in an overflow container.

Starting conditions of the electrodialysis:

Diluate 1: see below
Concentrate 1: =diluate 2:0.1% by weight aqueous solution of guanidinium dihydrogen phosphate
Concentrate 2: 0.1% by weight aqueous solution of guanidinium dihydrogen phosphate
Electrode rinse: 8% by weight aqueous solution of guanidinium dihydrogen phosphate

| parameter condition | diluate 1 | concentrate 2 |
| --- | --- | --- |
| Conductivity - start [mScm$^{-1}$] | 35 | 0.1 |
| Conductivity - finish [mScm$^{-1}$] | 0.2 | 59 |
| Guanidinium dihydrogen phosphate - start [% by weight] | about 11 | 0.1 |
| Guanidinium dihydrogen phosphate - finish [% by weight] | <0.3 | 23 |
| Iron - start [mg/kg] | about 3 | <0.1 |
| Iron - finish [mg/kg] | about 1 | <0.3 |

From the solution of concentrate 2, a technically pure guanidinium dihydrogen phosphate(content>99% by weight) can be isolated by subsequent crystallization which is suitable for customary use, for example in the production of flame guard equipment.

Example 5

1065 kg of a solution of guanidinium chloride from the production of a recombinant protein (diluate 1) were electrodialyzed for 60 hours in an apparatus as in the description of the claims with 2 membrane stacks each connected in series to 25 cell pairs having an effective cross-sectional area of 0.16 m$^2$ and a membrane spacing of 0.5 mm. A constant starting value of the current intensity of 60 ampere was set in both circuits, whereby the voltage necessary for this is automatically regulated in accordance with the respective resistance of the cell stack, but is limited to a maximum of 35 volts. With decreasing conductivity in the diluate 1 circuit, the current intensities corresponding to the maximum obtainable current intensity of 36 volts in the diluate 1 circuit are diminished in several steps. The product (concentrate 2) was collected in an overflow container. The electrodialysis was interrupted by customary rinse cycles as precipitates in diluate 1 diminished the flow rate to under 30% of the beginning value and was continued again after rinsing free.

Starting conditions of the electrodialysis:

Diluate 1: see below
Concentrate 1: =diluate 2: 5% by weight aqueous solution of guanidinium chloride
Concentrate 2: 5% by weight aqueous solution guanidinium chloride
Electrode rinse: 8% by weight aqueous solution of guanidinium dihydrogen phosphate Measuring protocol:

| time [h] | diluate 1 [kg] | [mScm$^{-1}$] | diluate 2 [% by weight] | [% by weight] | overflow [kg] | K-2 [% by weight] |
| --- | --- | --- | --- | --- | --- | --- |
| 0 | 1065 | 120 | 17.1 | — | 0 | — |
| 20,75 | 948 | 87 | 13.0 | 21.2 | 51.8 | 33.5 |
| 41,75 | 812 | 45 | 7.5 | 23.6 | 110.8 | 36.2 |
| 59,5 | 703 | 2 | 0.7 | 28.7 | 172.6 | 35.5 |

The average current yield was 57%.

From the solution of concentrate 2, a technically pure guanidinium chloride (content>98.5% by weight) can be isolated by subsequent crystallization which is suitable for renewed use, for example in the isolation of recombinant proteins.

We claim:

1. Method for recovering guanidine salts from an aqueous solution containing at least one impurity selected from the group consisting of proteins, sulfides, buffer salts, TRIS, EDTA and iron, comprising:

providing an electrodialysis cell having alternating diluate and concentrate compartments;

feeding said solution to the diluate compartment; subjecting said solution to electrodialysis; and recovering the concentrated guanidine salt from the concentrate compartment.

2. Method according to claim 1, characterized in that an aqueous guanidine salt solution is used as an electrode rinse.

3. Method according to claim 2, characterized in that the aqueous guanidine salt solution used as an electrode rinse is at least one solution selected from the group consisting of a guanidine phosphate solution and a guanidine sulfate solution.

4. Method according to claim 2, characterized in that a guanidine phosphate solution is used as an electrode rinse.

5. Method according to claim 1, characterized in that the current density in the electrodialysis is 200 to 1000 A/m$^2$ electrode surface.

6. Method according to claim 5, characterized in that the current density in the electrode dialysis is 300–700 A/m$^2$ electrode surface.

7. Method according to claim 5, characterized in that the voltage per cell pair during the electrodialysis is set to about 0.5 to 3 volts.

8. Method according to claim 7, characterized in that cell pairs are arranged in a membrane stack and said cell pairs per membrane stack number from 5 to 500.

9. Method according to claim 1, characterized in that the voltage per cell pair during the electrodialysis is set to about 0.5 to 3 volts.

10. Method according to claim 1, characterized in that cell pairs are arranged in a membrane stack and said cell pairs per membrane stack number from 5 to 500.

11. Method according to claim 1, characterized in that the pH-value is set to a value between 0 and 12 during the electrodialysis.

12. Method according to claim 1, characterized in that 2 or more membrane stacks are connected in series by using the concentrate from one membrane stack is used as a diluate in the following membrane stack.

13. Method according to claim 1, characterized in that the concentrated solution of the guanidine salt isolated by electrodialysis is subsequently subjected to a crystallization.

* * * * *